United States Patent
Covey et al.

(10) Patent No.: US 8,350,212 B2
(45) Date of Patent: Jan. 8, 2013

(54) ION OPTICS DRAIN FOR ION MOBILITY

(75) Inventors: Thomas R. Covey, Richmond Hills (CA); Bradley B. Schneider, Bradford (CA); John Vandermey, Georgetown (CA)

(73) Assignee: DH Technologies Development Pte. Ltd., Singapore (SG)

(*) Notice: Subject to any disclaimer, the term of this patent is extended or adjusted under 35 U.S.C. 154(b) by 93 days.

(21) Appl. No.: 12/722,863

(22) Filed: Mar. 12, 2010

(65) Prior Publication Data

US 2010/0237233 A1    Sep. 23, 2010

Related U.S. Application Data

(60) Provisional application No. 61/160,925, filed on Mar. 17, 2009.

(51) Int. Cl.
*H01J 49/26* (2006.01)

(52) U.S. Cl. .......................... 250/281; 250/282

(58) Field of Classification Search .................. 250/281, 250/282, 286, 287, 290, 292
See application file for complete search history.

(56) References Cited

U.S. PATENT DOCUMENTS

| | | | |
|---|---|---|---|
| 6,744,043 B2* | 6/2004 | Loboda | 250/287 |
| 2003/0089847 A1* | 5/2003 | Guevremont et al. | 250/282 |
| 2010/0108879 A1* | 5/2010 | Bateman et al. | 250/283 |

FOREIGN PATENT DOCUMENTS

GB    2443952 A    5/2008

OTHER PUBLICATIONS

International Search Report and Written Opinion in International Application No. PCT/U2010/027108 dated Jun. 17, 2010.

* cited by examiner

*Primary Examiner* — Kiet T Nguyen

(57) ABSTRACT

A sample analysis system incorporates an ion removal mechanism for removing residual ions from the sample analysis system. The ion removal mechanism can be included in an ion optics assembly, which connects an ion mobility filter to a mass analyzer. A sample to be analyzed by the sample analysis system may be entered into an ion mobility filter. The ion mobility filter filters the ions of the sample and passes the filtered group of ions to the ion optics assembly. The ion optics assembly transports the filtered group of ions to a mass analyzer where some or all of the ions in the group are detected. The ion removal mechanism then removes all or substantially all residual ions from the ion optics that were left over from the first filtered group before a second filtered group is passed through.

39 Claims, 13 Drawing Sheets

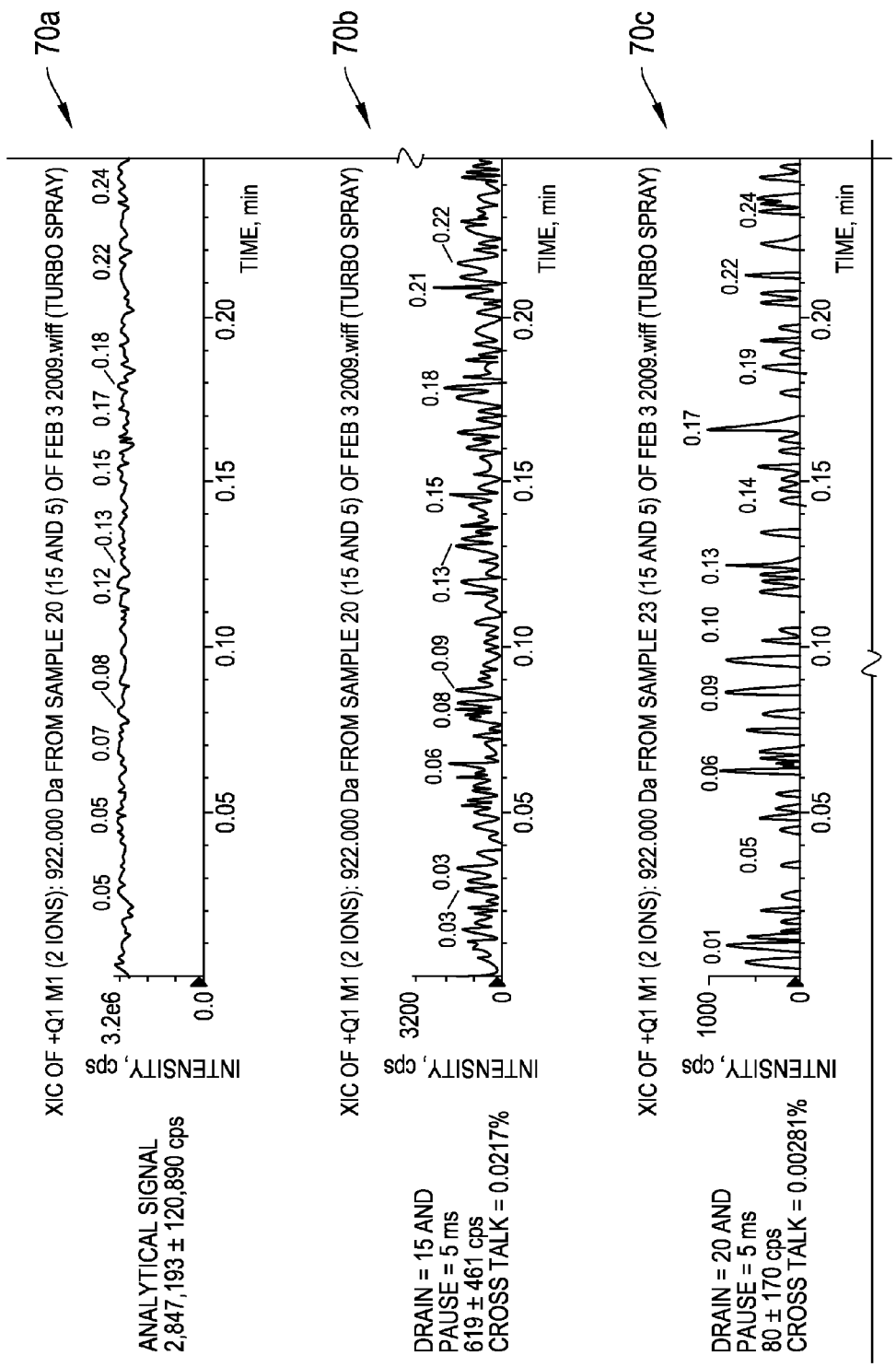
Fig. 10 (part 1)

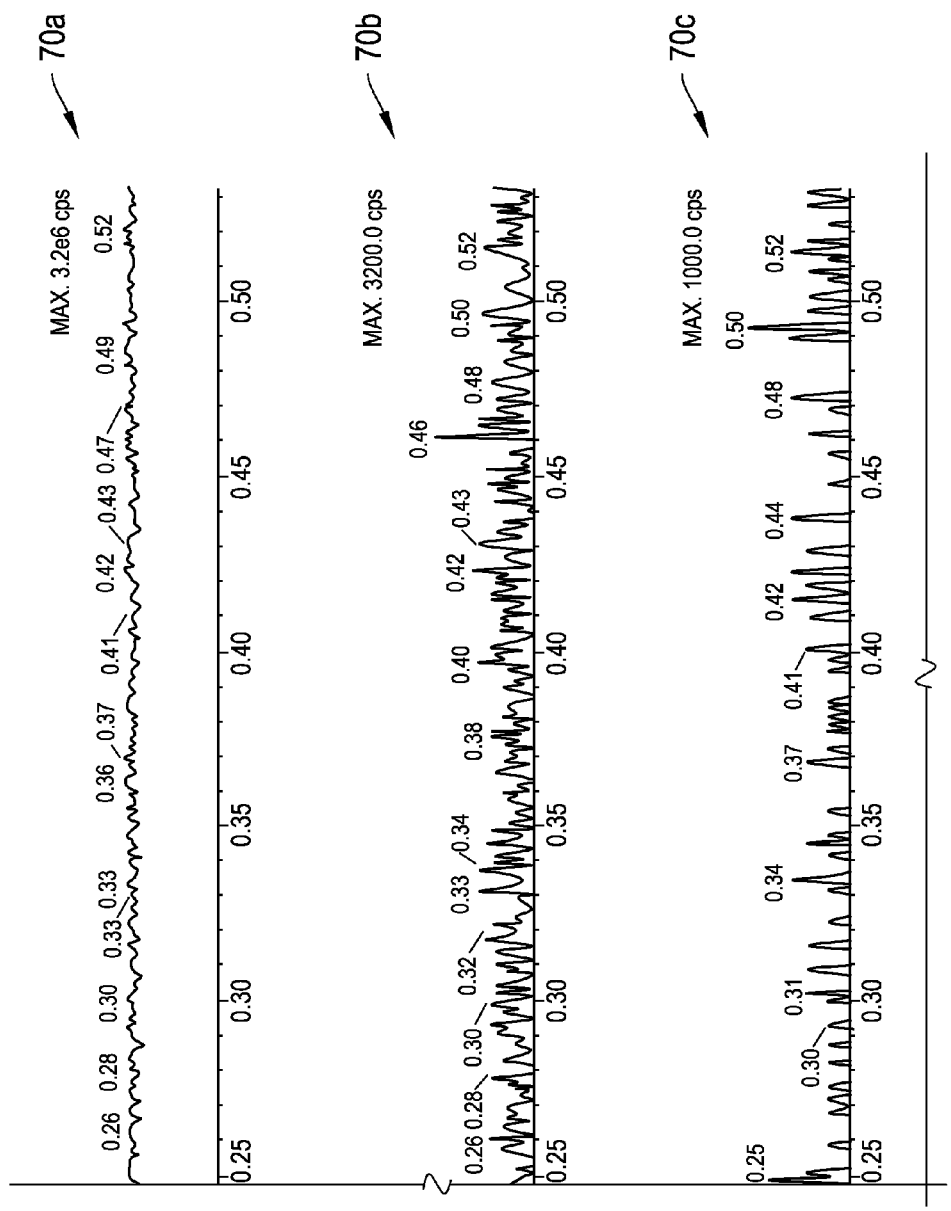
Fig. 10 (part 2)

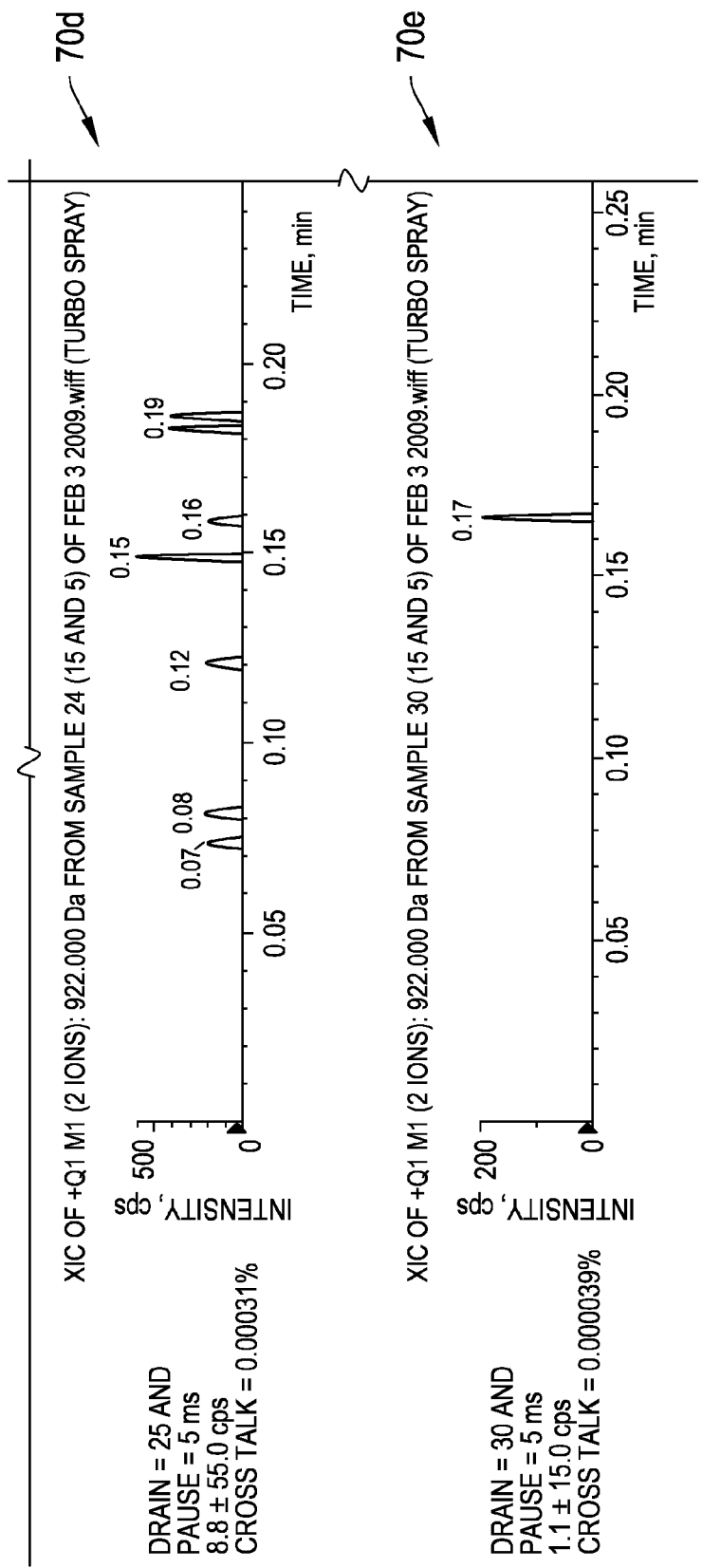
Fig. 10 (part 3)

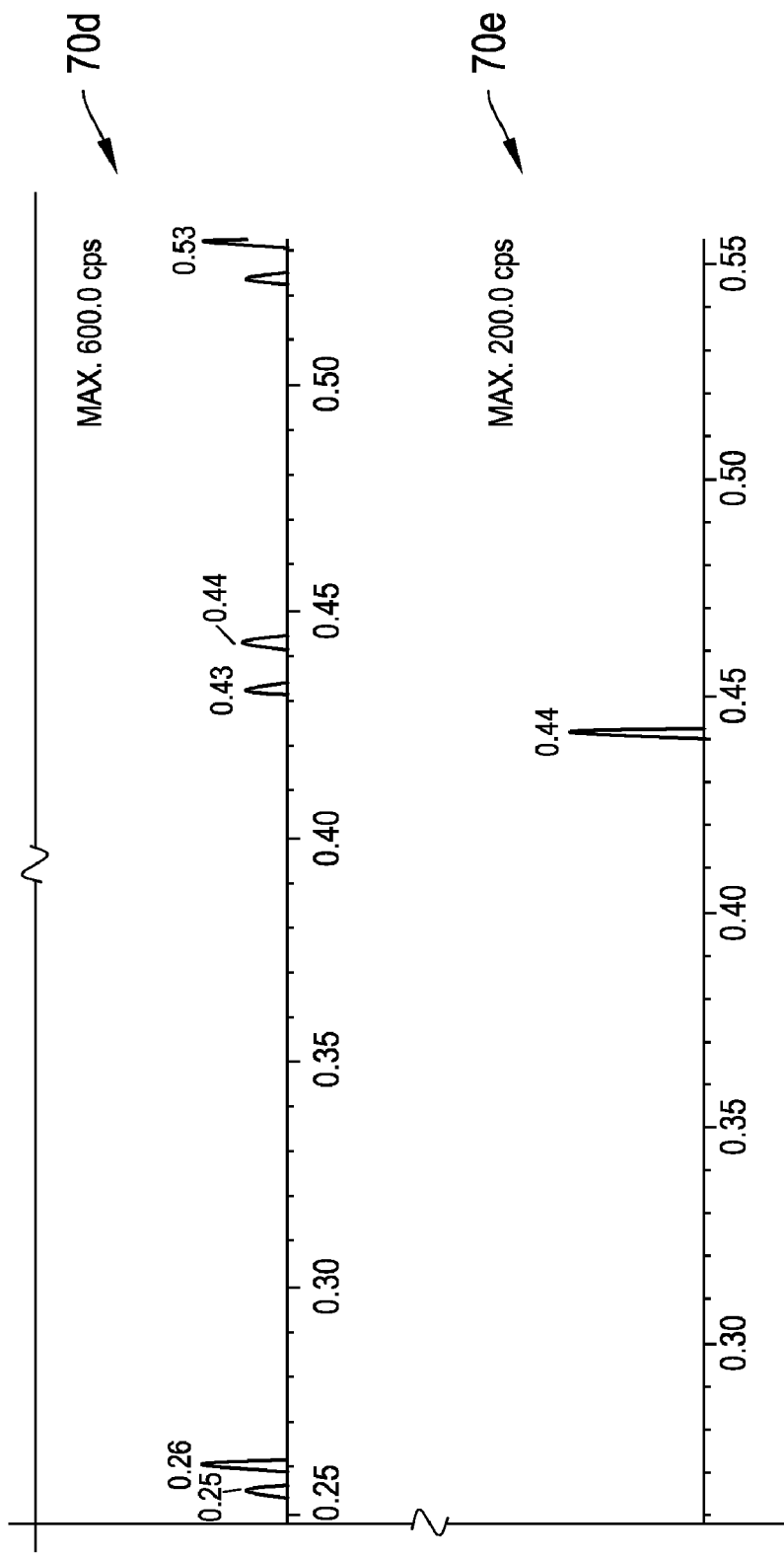
Fig. 10 (part 4)

ION OPTICS DRAIN FOR ION MOBILITY

REFERENCE TO RELATED APPLICATIONS

This application claims the benefit of U.S. Provisional Patent Application No. 61/160,925 filed Mar. 17, 2009 and entitled "Ion Optics Drain For Ion Mobility," the entirety of which is incorporated herein by reference.

INTRODUCTION

Ion mobility separation devices are commonly incorporated into mass spectrometer systems to provide added selectivity in analyzing sample compounds of interest. These systems allow for multiple different analytes to be monitored simultaneously. However, due to ion residence time, processing multiple different analytes can lead to the problem of chemical cross-talk. Chemical cross-talk occurs when ions from one sample contaminate data obtained on ions from another sample.

Accordingly, there is a need to remove ions from mass spectrometer systems to reduce or eliminate chemical cross-talk.

SUMMARY

The systems and methods described, inter alia, incorporate an ion removal mechanism in the sample analysis system for removing residual ions from the ion optics assembly. The ion removal mechanism can be included in the ion optics assembly, which connects an ion mobility filter to a mass analyzer. A sample to be analyzed by the sample analysis system may be entered into the ion mobility filter. The ion mobility filter filters the ions of the sample and passes the filtered group of ions to the ion optics assembly. The ion optics assembly transports the filtered group of ions to the mass analyzer where some or all of the ions in the group are detected. The ion removal mechanism then removes all or a substantial portion of the residual ions from the ion optics that were left over from the first filtered group before a second filtered group is passed through.

In one aspect, a sample analysis system includes a ion mobility filter for passing through a first group of ions; a mass analyzer for analyzing the first group of ions; and an ion optics assembly for transporting the first group of ions from the ion mobility filter to the mass analyzer, the ion optics assembly including an ion removal mechanism for removing residual ions from the ion optics assembly.

The sample analysis system can include a controller operatively coupled to one of the ion mobility filter, the mass analyzer and the ion optics assembly, or to a combination of all three, for controlling operation of each. The controller can include a timer for defining at least a first time period representative of a time for passing ions through the ion mobility filter and ion optics assembly, and at least a second time period representative of a time for operating the ion removal mechanism to remove residual ions from the ion optics assembly.

The ion mobility filter can be selected from one or more of low field mobility separators, high field mobility separators and differential mobility separators. In one aspect, the ion mobility filter can be one or more of Field Asymmetric Ion Mobility Systems (FAIMS), Differential Mobility Spectrometry (DMS), Ion Mobility Spectrometry (IMS), or Differential Mobility Analyzer (DMA).

In another aspect, the ion mobility filter can be located in a first pressure region, the mass analyzer can be located in a second pressure region different from the first pressure region, and the ion optics assembly can be located in a third pressure region having a pressure intermediate to the pressures in the first and second pressure regions. The third pressure region can include a plurality of different pressure regions.

In one aspect, the ion optics assembly can be one or more of a multipole array, ring guide, ion funnel, or travelling wave device.

In another aspect, the ion removal mechanism includes a power supply for applying a DC potential to at least two poles of the multipole array configured to remove residual ions from the ion optics assembly. The ion removal mechanism can apply a DC potential to create an electric field between at least two of the poles of the multipole array to expel the residual ions away from the ion optics assembly.

In yet another aspect, the ion removal mechanism includes at least one electrode in communication with a power supply for generating a DC potential to remove residual ions from the ion optics assembly. The ion removal mechanism can generate a DC potential to create an electric field that expels the residual ions radially out of the ion optics assembly. The ion removal mechanism can also generate a DC potential to create an axial electric field that expels residual ions out of the ion optics assembly. The at least one electrode can be one or more of a LINAC, resistive ion guide, lens electrode stack, ion funnel, or traveling wave ion guide.

In one aspect, the ion removal mechanism includes at least one electrode in communication with a power supply for generating a DC potential to accelerate ion motion through the ion optics. In another aspect, the controller is in communication with the ion removal mechanism for decreasing or removing the RF potential within the ion optics assembly to de-focus the ions and remove the ions from the ion optics assembly.

In one process, a method for analyzing a sample includes removing residual ions from an ion optics assembly; filtering a first group of ions using an ion mobility filter; transporting the first group of ions from the ion mobility filter to a mass analyzer using the ion optics assembly; and analyzing the first group of ions using the mass analyzer. Filtering the first group of ions and transporting the first group of ions can occur during a first period of time; removing residual ions from the ion optics assembly can occur during a second time period; and the ion mobility filter can filter a second group of ions and the ion optics assembly can transport the second group of ions from the ion mobility filter to the mass analyzer during a third time period.

In another process, a method for analyzing a sample includes: a) selecting, based on ion mobility, a first portion of ions and transmitting, using an ion optics assembly, the first portion of ions to a mass analyzer during a first time period; b) selecting, based on ion mobility, a second portion of ions and transmitting, using the ion optics assembly, the second portion of ions to the mass analyzer during a second time period; and c) emptying residual ions from at least a portion of the ion optics assembly during a third time period, the third time period occurring between the first and second time periods. The steps a) through c) can be iteratively repeated.

These and other features of the applicant's teachings are set forth herein.

DRAWINGS

The foregoing and other objects and advantages of the invention will be appreciated more fully from the following further description thereof, with reference to the accompanying drawings. The skilled person in the art will understand that the drawings, described below, are for illustration purposes only. The drawings are not intended to limit the scope of the applicant's teaching in any way.

FIG. 10 depicts plots of analytical signal data for varying drain times in relation to FIG. 9.

DESCRIPTION OF VARIOUS EMBODIMENTS

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art. For example, the illustrated system depicts ion removal in the ion optics, however, ion removal may be in an ion source, a mobility separation device, a conduit from an ion source, a mass analyzer cell or other locations within a mass spectrometry system.

Figure 1:
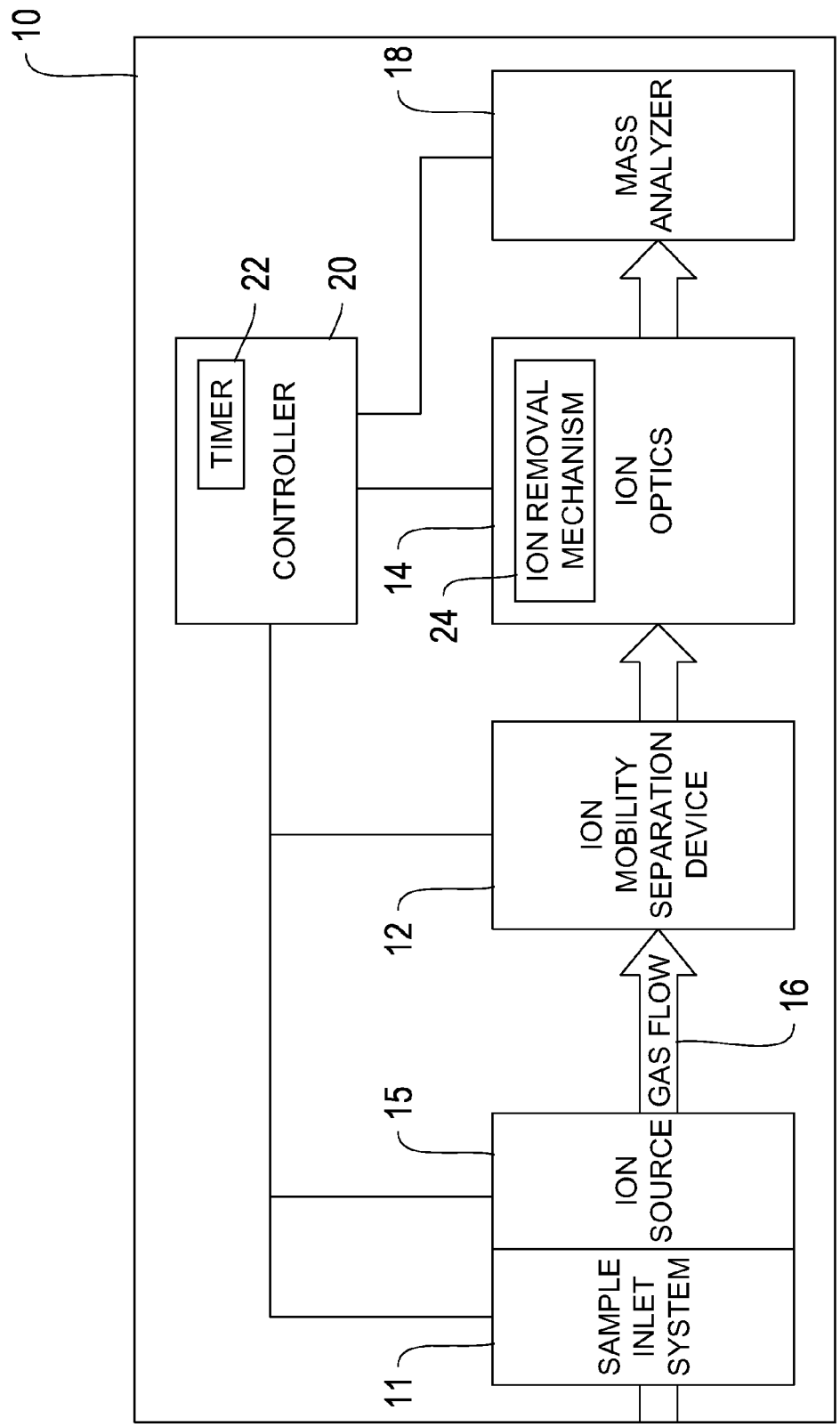
FIG. 1 depicts a schematic view of a mass spectrometer system according to an illustrative embodiment of the invention.

FIG. 1 depicts a schematic view of a mass spectrometer system 10. The depicted mass spectrometer system 10 comprises a sample inlet system 11, an ion source 15, an ion mobility separation device 12, instrumental optics 14, an ion removal mechanism 24, a mass analyzer 18, a controller 20, and a timer 22. The controller 20 can be connected to the sample inlet system 11, the ion source 15, the ion mobility separation device 12, the instrumental optics 14, and the mass analyzer 18.

The sample inlet system 11 can be any suitable sample inlet system known to one of skill in the art. The sample inlet system 11 is connected to ion source 15. The ion source 15 can be integrated with the inlet system 11 or can be separate from inlet system 11 and can be any suitable ion source known to one of skill in the art. For example, the two elements 11 and 15 can comprise an electrospray source with the ability to generate ions from a sample analyte dissolved in solution. Other example arrangements of the sample inlet system 11 and the ion source 15 are that of atmospheric pressure chemical ionization (APCI), atmospheric pressure photo-ionization (APPI), direct analysis in real time (DART), desorption electrospray (DESI), atmospheric pressure matrix-assisted laser desorption ionization (AP MALDI), multimode ionization sources, or configurations with multiple inlet systems and/or sources. However, any suitable sample inlet system and ion source can be used.

In certain embodiments, a sample compound is inserted into the mass spectrometer system 10 through sample inlet system 11. Gas flow 16 transports the sample from the sample inlet system 11 and ion source 15 through the ion mobility separation device 12. Those with skill in the art will understand that it is common to include a counter-current gas flow in the region between the ion source and the gas flow 16. The counter current gas flow (Curtain Gas) serves to decluster ions and prevent neutrals from entering the vacuum system. The ion mobility separation device (also know as an ion mobility filter) 12 separates a desired group or groups of ions from the sample based on the mobility, or velocity of ion species through a gas. The mobility of a particular ion species is dependent upon a number of parameters including size and shape. The ion mobility device 12 allows for separating isobaric compounds in time so that different ions with identical masses can be differentiated prior to a mass analyzer, such as the mass analyzer 18 of system 10. It will be appreciated that the ion mobility separation device used in the mass spectrometer system 10 of FIG. 1 may be any ion mobility device known to one of skill in the art (e.g., Field Asymmetric Ion Mobility Systems (FAIMS), Differential Mobility Spectrometry (DMS), Ion Mobility Spectrometry (IMS), Differential Mobility Analyzer (DMA), high-field, low-field, etc.). The controller 20 is coupled to ion mobility device 12 and can control the mobility filter settings to select for a particular ion species from the sample. Once the desired ion species is filtered by the ion mobility device, the filtered group of ions is passed to the ion optics 14.

The ion optics assembly 14 can use RF fields to focus the ions on to an ion optical path and direct the ions toward the mass analyzer 18. It will be appreciated that the ion optics assembly used in system 10 may be made up of any ion optics known to one of skill in the art (e.g., multipole array, ring guide, resistive ion guide, ion funnel, travelling wave ion guide.). The depicted ion optics assembly 14 comprises an ion removal mechanism 24 to remove residual ions from the ion optics assembly. The controller 20 is coupled to the ion optics assembly 14 and ion removal mechanism 24, and can control the application of RF and DC potentials to both.

After exiting the ion optics assembly 14, the ions travel via ion optical path to mass analyzer 18 where the ions are separated based on their mass-to-charge ratios (m/z) and detected. The detected ion data can be stored in memory and analyzed by a computer or computer software (not shown). The controller 20 is coupled to mass analyzer 18 to control the operation thereof.

The controller 20 of FIG. 1 comprises a timer 22. In various embodiments, the timer 22 can be used to define and synchronize time periods for functional operation of mass spectrometer system 10. For example, timer 22 can define one or more specific time periods for passing ions through the ion mobility separation device 12 and the ion optics 14, as well as one or more specific time periods for operating the ion removal mechanism 24 for removing residual ions from the ion optics assembly. During operation of mass spectrometer system 10, the plurality of operational time periods defined by timer 22 can occur in various combinatorial sequences. In various embodiments, three distinct time periods are defined by timer 22. A first time period is defined for selectively filtering a first group of ions and transmitting the first group of ions, via ion optics assembly 14, to the mass analyzer 18. A second time period is defined for selectively filtering a second group of ions and transmitting the second group of ions, via ion optics assembly 14, to the mass analyzer 18. A third time period is defined for emptying residual ions from the ion optics assembly 14, wherein the third time period occurs between the first and second time periods. In various embodiments, the sequence of the three time periods defined by time 22, and described above, occur iteratively during operation of mass spectrometer system 10.

Figure 2:
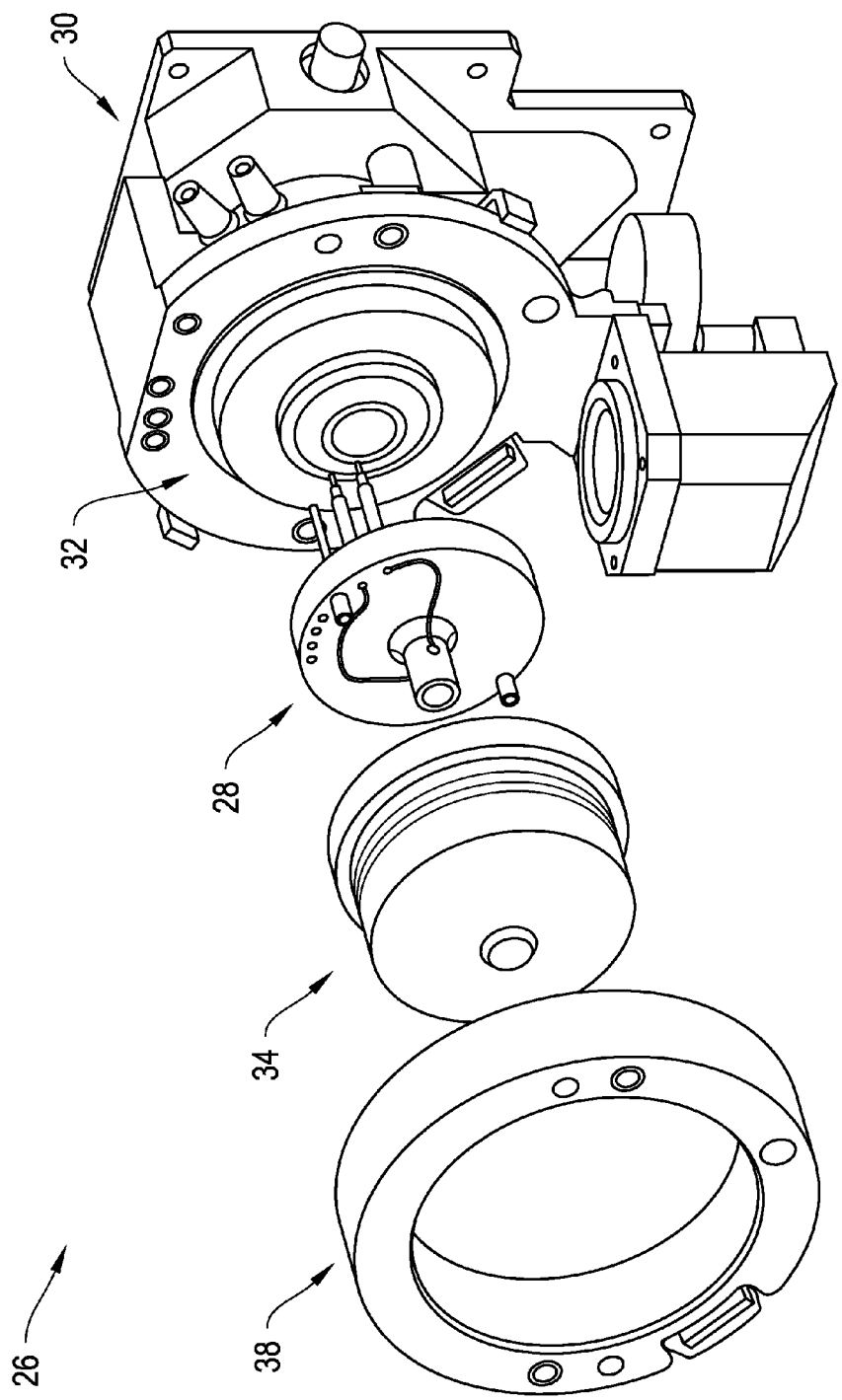
FIG. 2 depicts an exploded view of a mobility interface to a mass spectrometer system suitable for use in the system of FIG. 1.

FIG. 2 depicts an exploded view of a mass spectrometer system 26 suitable for use in the system of FIG. 1 as system 10. Mass spectrometer system 26 comprises a DMS mobility cell 28, the inlet of a combined ion optics/mass analyzer device 30, an orifice 32, a curtain plate 34 and a source extension ring 38. The DMS mobility cell 28 is an example of an ion mobility separation device suitable for use as element 12 of system 10 in FIG. 1. DMS mobility cell 28 connects to the ion optics/mass analyzer device 30 and is separated by orifice 32. Curtain plate 34 fits over DMS mobility cell 28 and fastens onto orifice plate 32. The source extension ring 38 connects an ion source, such as ion source 15 of FIG. 1 (not shown in FIG. 2), to the system. In the example shown in FIG. 2, the source extension ring 38 provides the correct spacing between the ion source 15 and the curtain plate 34. Additionally, as depicted in FIG. 2, the source extension ring 38 provides a path for delivering potentials and gas flows to the ion source 15. The curtain plate 34 directs the curtain gas flow towards the ion source 15. A high-purity curtain gas (e.g., $N_2$) flows between curtain plate 34 and orifice 32 and aids in keeping the mass spectrometry device 10 clean by dissolving and evacuating large neutral particles.

Figure 3:
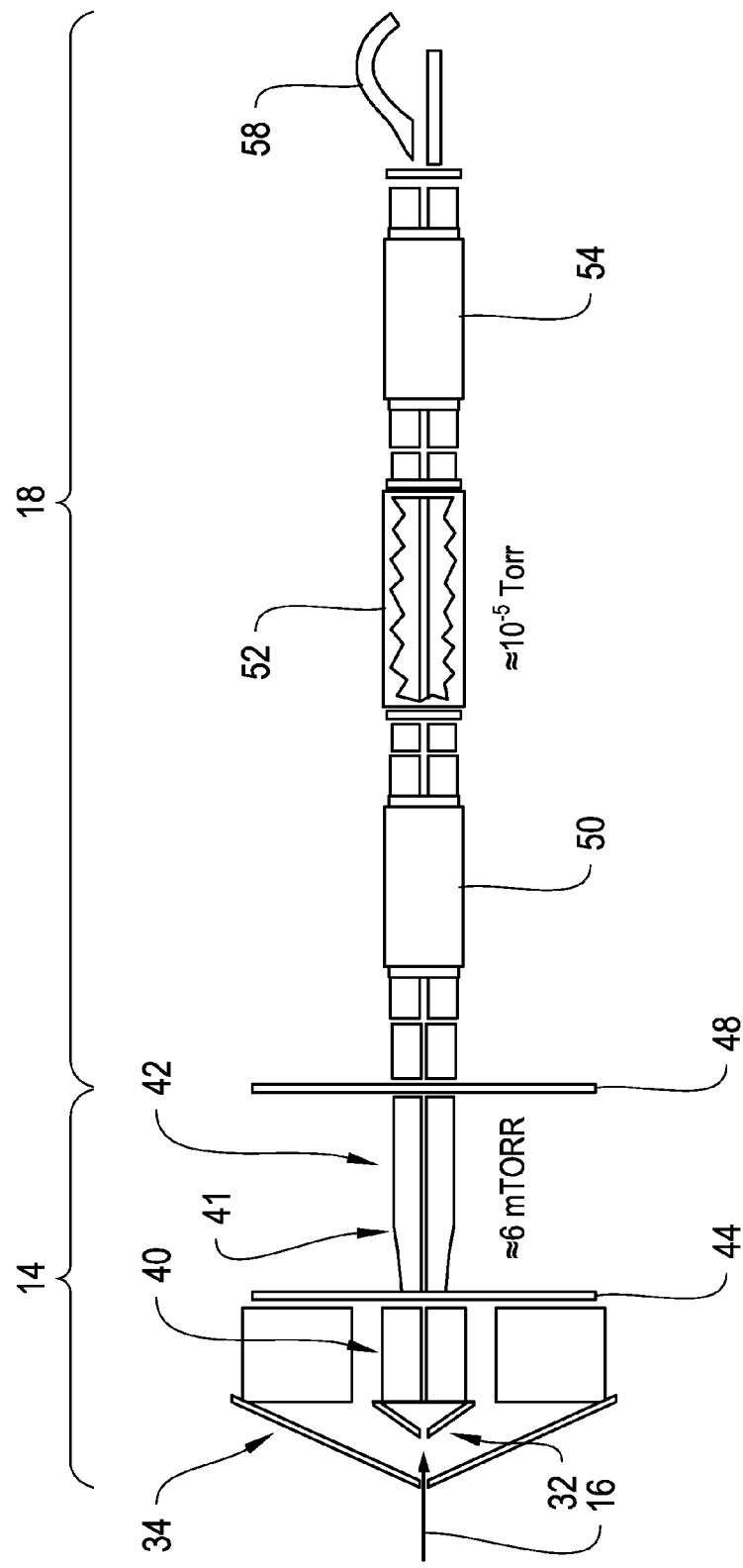
FIG. 3 depicts schematically the structure of the ion optics and mass analyzer suitable for use in the system of FIG. 1.

FIG. 3 depicts schematically, and in more detail, the structure of one example of the ion optics and mass analyzer suitable for inclusion in the system 26 of FIG. 2 as element 30. FIG. 3 shows an API 5000 mass spectrometry system modified to include an ion removal mechanism 41, suitable for use as ion removal mechanism 24 of system 10 in FIG. 1. The API 5000 is one type of system that can utilize an ion removal mechanism for removing ions. FIG. 3 includes instrumental optics 14, mass analyzer 18, ion removal mechanism 41, curtain plate 34 and orifice 32. Instrumental optics 14 comprises QJet RF ion guide 40 and Q0 RF ion guide 42 separated by IQ0 lens 44. The QJet RF ion guide 40 is used to capture and focus ions using a combination of gas dynamics and radio frequency fields. The QJet 40 transfers ions from the orifice 32 to subsequent ion optics such as the Q0 RF ion guide 42. The Q0 RF ion guide 42 transports ions through an intermediate pressure region (shown as ≈6 mTorr in FIG. 3) and delivers ions through the IQ1 lens to the high vacuum chamber containing the mass analyzer 18. As demonstrated in FIG. 3, the mass analyzer 18 region comprises Q1 Quadrupole analyzer 50, Q2 Quadrupole collision cell 52, Q3 Quadrupole analyzer 54 and CEM detector 58. The illustrated instrumental optics 14 comprising QJet RF ion guide 40 and Q0 RF ion guide 42 are an example of optics that can be used in ion optics assembly 14 of FIG. 1. However, in some embodiments the elements 40, 42 can be used individually, in combination with other types of ion optics, or not used in mass spectrometer system 10 at all. In some embodiments, QJet ion guide 40 and Q0 ion guide 42 can be capacitively coupled to either Q1 50 or Q3 54. In some embodiments, the ion optics 14 and mass analyzer 18 can include one or more pressure regions, separated by apertures, operating in a range of pressures. For example, in the system of FIG. 3, QJet 40 is set at 2.5 Torr, Q0 42 is set at 6 mTorr and mass analyzer 18, comprising Q1 50, Q2 52 and Q3 54, is set at $10^{-5}$ Torr. It will be apparent to those of skill in the art that Q2 52 comprises a collision cell for fragmenting ions, and the gas pressure within the Q2 cell may be substantially higher than the pressure in Q1 50 and Q3 54.

Ion mobility device 12, comprising DMS mobility cell 28 of FIG. 2, typically operates at atmospheric pressure (~760 Torr). The controller 20 can be used to adjust the pressure in the various regions.

In FIG. 3, the ion removal mechanism 41 comprises the electrodes of the Q0 RF ion guide 42. In this embodiment, the electrodes of Q0 RF ion guide 42 are electrically connected to at least one power supply, such as power supply 61, shown in FIG. 4, that can apply a voltage to the electrodes to create an electric field having a vector direction selected to move ions out of the ion optics assembly. In some embodiments, the electric field created by ion removal mechanism 41 removes ions by overcoming the focusing field within the ion optics and pushing the ions out of focus. In some embodiments, the ion removal mechanism 41 removes ions by eliminating the focusing field within the ion optics and allowing ions to drain out. As a result of defocusing the ions, the ions can collide with the electrodes within the ion optics or can be carried out of the ion optics by a gas flow or a combination of both. The power supply 61 can operate under the control of the controller 22, which can be a programmable controller unit capable of controlling and applying the electric field that removes ions from the ion optics. In some embodiments, ion removal mechanism 41 can be separate from Q0 42 (e.g., peripheral electrodes), integrated with QJet 40, mass analyzer 18, or any other part of mass spectrometer system 10 of FIG. 1. In some embodiments, the ion removal mechanism 41 can include controller 20 and timer 22 to control application of a voltage to electrodes within the mass spectrometer device 10. In some embodiments, ion removal mechanism 41 can include software on a computing device which can be configured to instruct controller 20 to control application of RF and DC potentials on mass spectrometry components. For example, software can be programmed to control the RF and DC voltages on the ion optics 14. Other examples of possible configurations for ion removal device 41 are described in more detail below with respect to FIG. 4-7.

The ion mobility separation device of FIG. 2 comprises a DMS mobility cell 28 sealed onto the vacuum restricting orifice of the mass spectrometer system. The vacuum draw into the orifice establishes a carrier gas flow through the DMS cell. Therefore, the residence time within the DMS cell is directly proportional to the volume of the cell and inversely proportional to the flow rate of the carrier gas flow. For example, the residence time for a DMS mobility cell as illustrated in FIG. 2 may be ≈6 ms. In certain embodiments, the ion residence time in the mobility separation device can be accounted for by using timer 22 of controller 20 to add a pause time into the instrumental method to allow the gas flow to restabilize the ion current through the mobility cell when the mobility conditions are changed. While the example given here was for a DMS with ≈6 ms residence time, it will be apparent to those of skill in the art that the residence time within the mobility cell may vary substantially for alternate mobility techniques. As an example, the residence time in a DMA may be on the order of 1 ms or less and the residence time within a cylindrical FAIMS mobility analyzer may be on the order of 100 ms.

Ions travelling through the mobility cell are carried into the orifice, where a vacuum expansion occurs as a result of the pressure differential on either side of the orifice. In FIG. 3, the ions travel from an atmospheric pressure region in the mobility filter to a 2.5 Torr pressure region in the QJet ion guide 40, and then to a 6 mTorr pressure region in the Q0 ion guide 42. As ions travel through the ion optics assembly 14, the gas flow 16 can become disrupted, particularly in the Q0 ion guide 42, causing, among other things, ion band spread. Ion band spread occurs when certain portions of ions travel with different velocities through the ion optical assembly 14. In operation, the difference in ion velocities can provide substantial spread in the residence time for a group of ions within an RF multipole, such that residual ions may be left within the multipole after the majority of ions have passed through. Under some conditions, the residence time of residual ions within the ion optics can be relatively long (i.e., greater than 100 ms), thus requiring long pause times to account for the residual ions, which resultantly compromise the duty cycle of devices such as mass spectrometer system 10. Additionally, the residual ions can cause chemical cross-talk when they mix with subsequent samples passing through the ion optics, causing errant data results.

In various embodiments, an ion removal mechanism, such as ion removal mechanism 24 of FIG. 1, removes or substantially reduces residual ions from the ion optics, thereby preventing or reducing chemical cross-talk between samples. Because ion removal can occur very quickly, it can take place during an instrumental pause time, such as the pause time used to account for residence time in the ion mobility separation device as discussed above, using timer 22. While not to be limited by theory, it is understood that ion removal mechanism 24 can remove residual ions from mass spectrometer system 10 by creating a destabilizing electric or magnetic field within the device. The destabilizing field can alter the field within the mass spectrometer device used during standard operation and can defocus ions or overcome a focusing field within the device. As previously described, the ion removal mechanism 24 can include software on a computing device, instrumental ion optics such as Q0 RF ion guide 42, or any other suitable combination that can be used to defocus ions within a mass spectrometry device. In some embodiments controller 20 can be a suitable computing device for storing and executing software to control ion removal mechanism 24.

Aspects of the applicant's teachings may be further understood in light of the following examples, which should not be construed as limiting the scope of the applicant's teachings in any way. Additionally, teachings from each example can be combined without departing from the scope of the invention.

EXAMPLE 1

Figure 4:
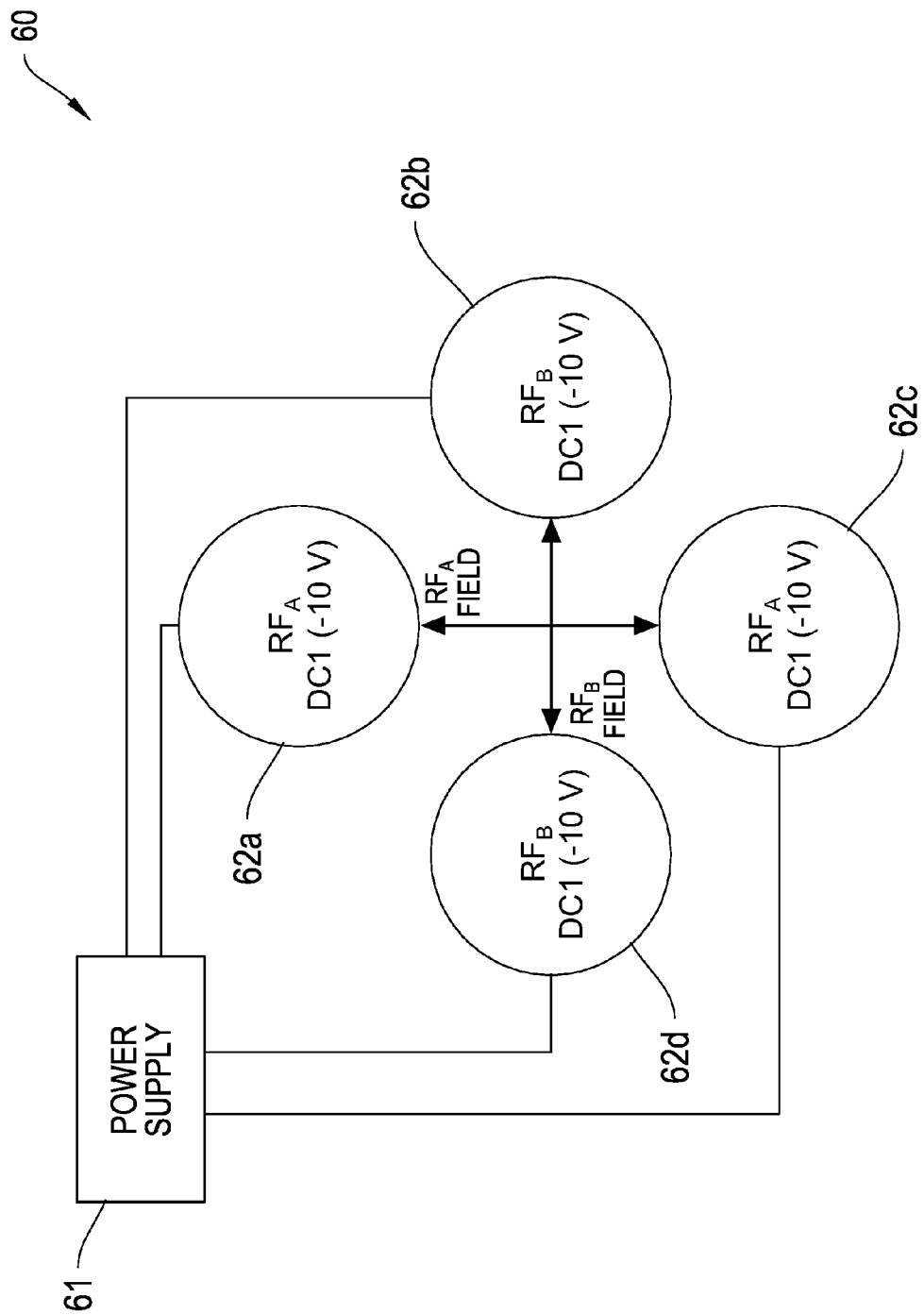
FIG. 4 depicts a cross sectional view of a quadrupole ion optics array suitable for inclusion in the system of FIG. 3.

FIG. 4 depicts a cross sectional view of a quadrupole ion optics array 60 suitable for inclusion in the instrumental optics of FIG. 3. Array 60 is depicted as a quadrupole, but can be an octapole, hexapole or any other multipole as known in the art. For the purposes of this exemplary illustration, ion optics array 60 is a Q0 RF ion guide, such as Q0 ion guide 42 in FIG. 3, but it will be appreciated by those of ordinary skill in the art that optics array 60 could be a QJet RF ion guide, such as QJet ion guide 40 of FIG. 3, or one of various other ion optics configurations known in the art. Ion optics array 60 comprises quadrupole rods 62A-D. Power supply 61 is connected to rods 62A-D and can apply RF and DC voltages to each rod. Power supply 61 can be controlled by controller 20 of FIG. 1 to apply a range of distinct DC and RF voltages to each of the rods in ion optics array 60. In this illustrative example, when the Q0 ion optics 60 are operating to transport and focus ions to an ion optical path, each rod has a −10 volt DC voltage applied to it. Rods 62A and 62C have identical RF voltages ($RF_A$) applied to each, creating $RF_A$ field between the rod pair. Rods 62B and 62D have identical RF voltages ($RF_B$) applied to each, creating $RF_B$ field between the rod pair. The RF fields within the quadrupole array can be combined with superimposed DC voltages to focus ion within the optics array 60. Optics array 60 can be configured to create an ion removal mechanism, such as ion removal mechanism 24 of FIG. 1. A possible configuration is described in more detail with respect to FIG. 5 in Example 2. In various embodiments, ion removal mechanism 24 can eliminate, or substantially eliminate residual ions by causing the ions to collide with one of the quadrupole rods 62A-D or fly out between the quadrupole rods as a result of gas flow.

EXAMPLE 2

Figure 5:
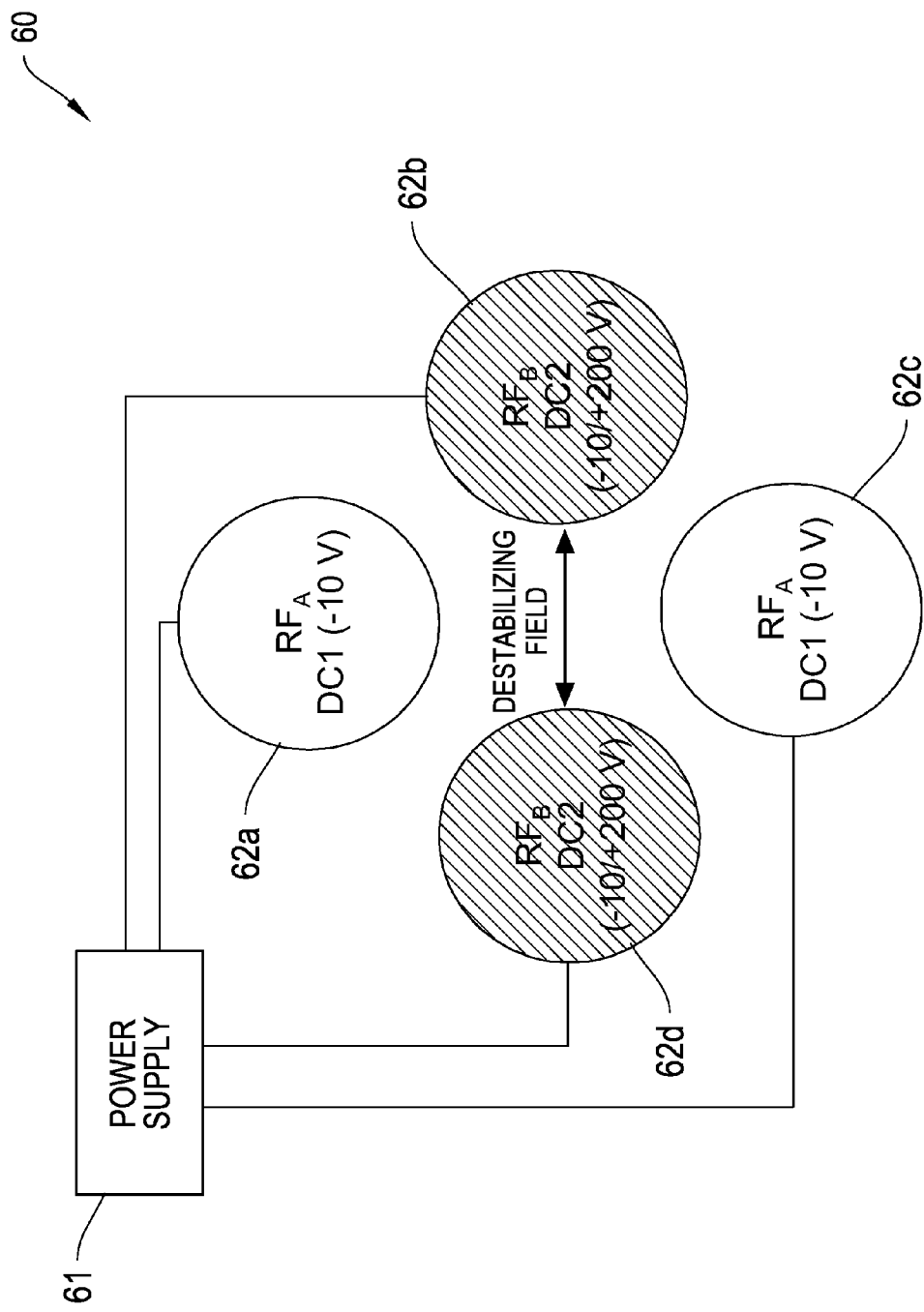
FIG. 5 depicts a cross sectional view of the quadrupole ion optics array and an exemplary configuration of an ion removal mechanism.

FIG. 5 depicts ion optics array 60 during an ion draining period. In FIG. 5, the optics array 60 and power supply 61 are configured to create an ion removal mechanism, such as ion removal mechanism 24 of FIG. 1. In FIG. 5, the ion removal mechanism applies a DC potential to quadrupole rods 62B and 62D that is increased relative to the other poles (i.e., +200 V) during the drain period defined by timer 22. This applies an unbalanced resolving DC potential onto the quadrupole electrodes. The DC potential can be controlled by controller 20 (not shown in FIG. 5) and applied by power supply 61 to rods 62B and 62D. The increased DC potential applied to quadrupole rods 62B and 62D creates a destabilizing electric field between the poles to overcome the focusing field applied by optics array 60 and expel ions, including residual ions, away from the ion optical path.

EXAMPLE 3

Figure 6:
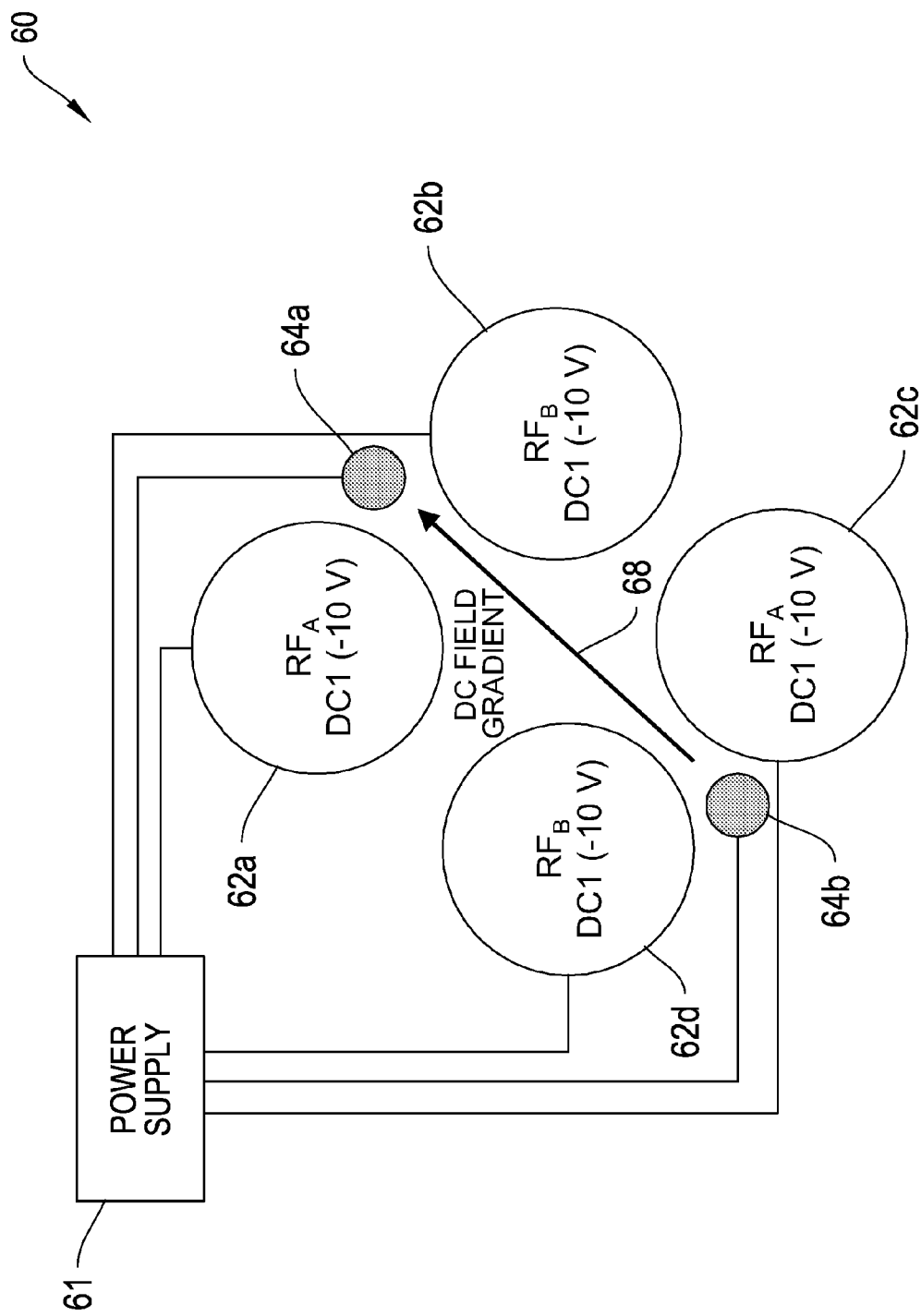
FIG. 6 depicts a cross sectional view of the quadrupole ion optics and another possible configuration of an ion removal mechanism using drain electrodes.

FIG. 6 depicts a cross sectional view of the quadrupole ion optics 60 in another possible configuration. In FIG. 6, there are drain electrodes 64A and 64B, which are separate from the quadrupole array 60, that are placed between quadrupole rods 62A and 62B, and 62C and 62D, respectively. It will be appreciated by one of ordinary skill in the art that any suitable number or type of drain electrodes can be used without departing from the scope of the invention. It will also be apparent that power supply 61 may comprise one or more different power supplies. In this example, the drain electrodes 64A and 64B make up an ion removal mechanism, such as ion removal mechanism 24 of FIG. 1. During a draining period defined by timer 22, power supply 61 coupled to the drain electrodes can apply a DC potential to drain electrodes 64A and 64B creating a DC field gradient 68 between them. The DC field gradient 68 can act as a destabilizing field to overcome the focusing field created by optics array 60 and radially eject any ions, including residual ions, away from the ion optical path and out of the ion optics. The magnitude of the electric field and length of time that it must be applied depends upon the pressure within the RF multipole and the mobility of the ion to be ejected. In various embodiments at least one electrode (one example of this may be a linear accelerator such as a LINAC) is placed in close proximity to the ion optics and makes up an ion removal mechanism suitable for use as ion removal mechanism 24 in FIG. 1. The electrodes can be used for accelerating ions through an RF multipole or expelling residual ions from the RF multipole. A power supply connected to the electrodes can apply a DC potential to the electrodes, causing the electrodes to generate an electric field to axially expel ions, including residual ions, out of the ion optics. The electrodes can also accelerate ions to reduce the residence time within the ion optics and thereby reduce or substantially eliminate ion beam spreading.

EXAMPLE 4

Figure 7:
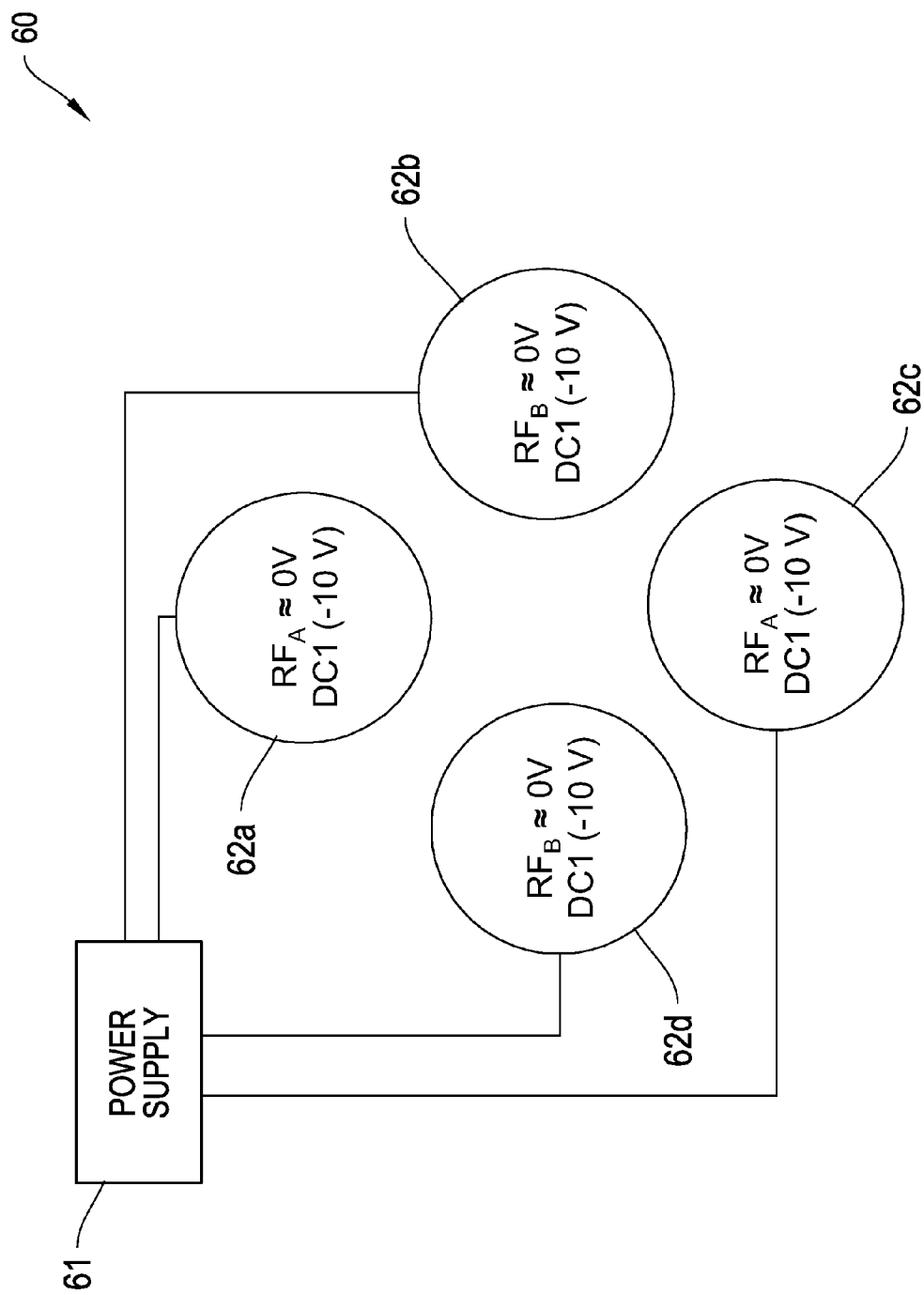
FIG. 7 depicts a cross sectional view of the quadrupole ion optics and another possible configuration of an ion removal mechanism.

FIG. 7 depicts a cross sectional view of the quadrupole ion optics 60 in another illustrative configuration. In the illustrative example of FIG. 7, an ion removal mechanism, suitable for use as ion removal mechanism 24 of FIG. 1, can be created by coupling controller 20 to power supply 61 and to quadrupole rods 62A-D, to control the RF potential applied to each. In this example the ion removal mechanism operates by decreasing the RF potentials, $RF_A$ and $RF_B$ to approximately 0 volts on the quadrupole rods 62A-D. As described above, software on a computing device can be programmed to instruct controller 20 to remove or reduce the RF field in ion optics 60 during defined time periods. In various embodiments, the RF potential on the quadrupole rods is controlled through the Q1 50 and Q3 54 analyzers of FIG. 3, which are capacitively coupled to the quadrupole rods 62A-D.

During normal ion transport mode, the RF potentials applied to the quadrupole rods 62A-D create RF fields, $RF_A$ and $RF_B$, which serve to focus and direct the ions in an ion optical path. In this illustrative example, as a result of reducing the RF potential on each rod 62A-D, the $RF_A$ and $RF_B$ fields are substantially or completely eliminated, thus removing the focusing field applied to the ions with in the ion optics 60. The lack of focusing fields $RF_A$ and $RF_B$ causes ions within the optics to collide with one of the quadrupole rods 62A-D, fly out between the quadrupole rods as a result of gas flow, or be removed from the ion optics 60 in another manner. During an ion drain period defined by timer 22, residual ions residing within the ion optics can be scattered from the ion optical path as a result of removing the RF potential from the quadrupole rods 62A-D, and subsequently removed from the ion optics.

Figure 8:
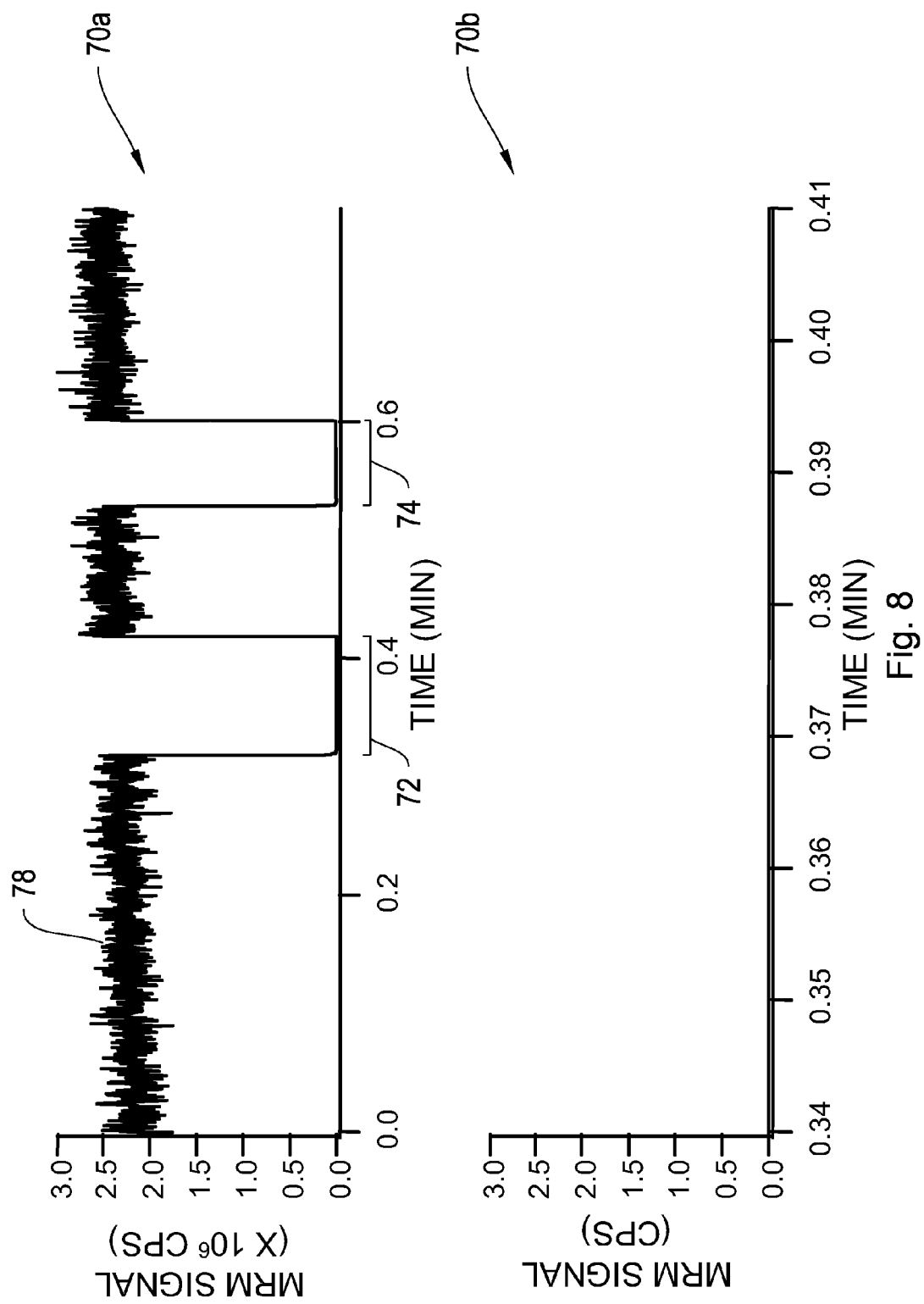
FIG. 8 depicts a plot of Multiple Reaction Monitoring data gathered using a device set-up as depicted in FIG. 5.

FIG. 8 depicts a plot of Multiple Reaction Monitoring (MRM) data gathered using a device set-up as depicted in FIG. 5 and using a QJet ion optic. Plot 70A of FIG. 8 shows MRM signal 78 for a reserpine sample (indole alkaloid commonly used as an antipsychotic and antihypertensive drug) entered into an API 5000 mass spectrometer system suitable for use as system 10 of FIG. 1. At the start of data collection, a −10 volt DC potential is applied to each quadrupole rod 62A-D of FIG. 5. During time periods 72 (0.34 min to 0.41 min) and 74 (0.52 min to 0.6 min) in plot 70A, the power supply is switched by controller 20 to apply a DC potential of 200 volts to quadrupole rods 62B and 62D, before being returned to −10 volts. As shown in plot 70A the MRM signal is approximately 0.0 cps during time periods 72 and 74 when a 200 V DC voltage is applied to poles 62B and 62D in the device configuration displayed in FIG. 5. Plot 70B depicts a blow-up of time period 72 to demonstrate complete elimination of the MRM signal for reserpine ions. FIG. 8 expresses the effectiveness of the ion removal mechanism, as configured in FIG. 5, for removing residual reserpine ions from a QJet ion optics rod set operating at 2.5 Torr.

Figure 9:
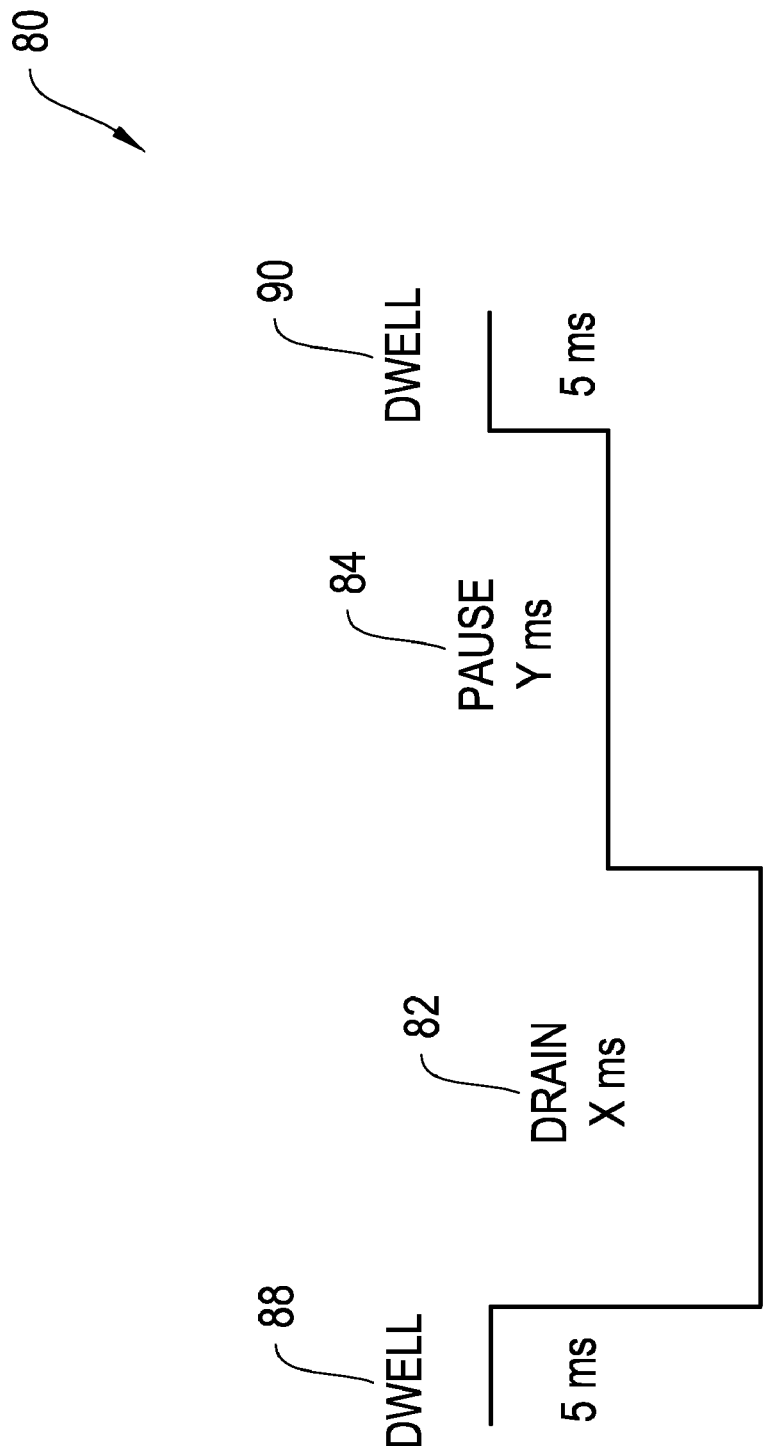
FIG. 9 depicts a timing diagram for operation of the device as depicted in FIG. 7.

FIG. 9 depicts a timing diagram 80 for operation of an ion removal mechanism such as removal mechanism depicted in FIG. 7. Timing diagram 80 comprises a drain time 82, pause time 84 and dwell times 88 and 90. In timing diagram 80, the dwell times are set to 5 ms while the drain time and pause time are variable. Table 1 shows settings applied to the DMS mobility cell of a mass spectrometer system, such as the system shown in FIG. 2. In row 1 of Table 1, the correct settings are given to maximize transmission of a particular ion species (i.e., m/z 922). Throughout this experiment, the mass spectrometer monitors the signal for ions with m/z 922 as measured in the first mass analyzer (Q1). In the first period of the scan table shown in Table 1, the mobility device is configured to apply the separation voltage with an amplitude of approximately 3000 V. Under these conditions, transmission for the ion of interest (m/z 922) is optimized with a compensation voltage (CV) of approximately 4.2 V. In experimentation, applying the correct settings to the mobility device resulted in a maximum intensity analytical signal. In row 2 of Table 1, the incorrect settings for transmission of m/z 922 ions are shown. With the incorrect settings applied to the mobility device, the analytical signal for m/z 922 ions should be eliminated completely as a result of no m/z 922 ions being transmitted by the mobility device. However, when rapidly switching between period 1 and period 2, an analytical signal for m/z 922 ions is still observed during period 2 as a result of cross talk within the ion optics, specifically within the Qjet RF ion guide 40 and the Q0 RF ion guide 42, as depicted in FIG. 3. Therefore, the signals obtained using the settings of row 2 represent cross-talk within the transfer ion optics of the mass spectrometer system.

TABLE 1

|   | m/z | Dwell (ms) | AC (V) | CV (V) |
|---|---|---|---|---|
| 1 | 922 | 5 | 3000 | 4.2 |
| 2 | 922 | 5 | 1500 | 30 |

To determine the effectiveness of the ion removal mechanism 24 as configured in FIG. 7, a drain period 82 was inserted prior to the instrumental pause time, as shown in FIG. 9, by timer 22. Settings from row 1 of Table 1 were applied during dwell time 88 resulting in maximum transmission of the ion species (m/z settings from row 2 were applied during dwell time 90). At the start of the drain period 82, Q1 and Q3 were set to 5 daltons and the mobility conditions for period 2 were set, thereby substantially removing (or reducing) the RF potential from quadrupole rods 62A-62D of FIG. 7, to drain the residual ions from the Q0 ion optics. Immediately after the defined drain period 82, the row 2 (cross-talk) m/z setting of table 1 was applied to the Q1 mass analyzer.

FIG. 10 depicts the results of the ion removal experiment described above. FIG. 10 shows plots of analytical signal data for varying drain times in relation to FIG. 9. FIG. 10 includes plots 70A-E which show signal intensity in counts per second (cps) vs. time (min). Plot 70A shows the intensity of the analytical signal being equal to 2,847,193+/−120,890 cps during maximum transmission of the ion species (Conditions defined by period 1 from Table 1). In plots 70B-E the pause time 84 of FIG. 9 is held constant at 5 ms, while the drain time 82 of FIG. 9 is varied between 15 and 30 ms. % Cross-talk is calculated for each drain time according to the equation below:

$$\% \ CrossTalk = \left(\frac{CrossTalk}{AnalyticalSignal}\right)(100\%)$$

As shown in plots 70B-70E, as the drain time 82 increases from 15 ms to 30 ms, essentially all of the residual ions are eliminated and the % cross-talk decreases substantially from 0.0217% to 0.000039%. Turning off the ion removal device completely, and using a default 20 ms pause time, the cross talk was approximately 3% for these experiments. Therefore, even with the lowest drain time depicted in FIG. 10 (15 ms), the measured cross talk was reduced by approximately 100× relative to the same hardware with no ion removal device. Thus, the above experiment demonstrates the effectiveness of the ion removal mechanism in removing residual ions from the ion optics and significantly reducing chemical cross-talk.

Those skilled in the art will know or be able to ascertain using no more than routine experimentation, many equivalents to the embodiments and practices described herein.

Accordingly, it will be understood that the invention is not to be limited to the embodiments disclosed herein, but is to be understood from the following claims, which are to be interpreted as allowed as broadly as allowed under the law.

What is claimed is:

1. A sample analysis system, comprising:
   an ion mobility filter for filtering and transmitting a first group of ions therethrough;
   a mass analyzer for analyzing the first group of ions; and
   an ion optics assembly for transporting the first group of ions from the ion mobility filter to the mass analyzer, and comprising an ion removal mechanism for removing residual ions from the ion optics assembly,
   wherein the ion mobility filter is coupled to a vacuum orifice inlet of the mass analyzer.

2. The system of claim 1 further comprising: a controller operatively coupled to the ion mobility filter, the mass analyzer and the ion optics assembly for controlling operation thereto.

3. The system of claim 2, wherein the controller comprises a timer for defining at least a first time period representative of a time for passing ions through the ion mobility filter and ion optics assembly, and at least a second time period representative of a time for operating the ion removal mechanism to remove residual ions from the ion optics assembly.

4. The system of claim 2, wherein the controller is in communication with the ion removal mechanism for decreasing the RF potential within the ion optics assembly to defocus the ions and remove the ions from the ion optics assembly.

5. The system of claim 1, wherein the ion mobility filter is selected from the group consisting of low field mobility separators, high field mobility separators and differential mobility separators.

6. The system of claim 1, wherein the ion mobility filter is selected from the group consisting of FAIMS, DMS, IMS, and DMA.

7. The system of claim 1, wherein the ion mobility filter is located in a first pressure region.

8. The system of claim 7, wherein the mass analyzer is located in a second pressure region different from the first pressure region.

9. The system of claim 8, wherein the ion optics assembly is located in a third pressure region having a pressure intermediate to the pressures in the first and second pressure regions.

10. The system of claim 9, wherein the third pressure region comprises a plurality of different pressure regions.

11. The system of claim 1, wherein the ion optics assembly is selected from the group consisting of multipole array, ring guide, ion funnel, and travelling wave device.

12. The system of claim 11, wherein the ion removal mechanism comprises a power supply for applying a DC potential to at least two poles of the multipole array configured to remove residual ions from the ion optics assembly.

13. The system of claim 12, wherein the ion removal mechanism applies a DC potential to create an electric field between at least two of the poles of the multipole array for expelling the residual ions away from the ion optics assembly.

14. The system of claim 1, wherein the ion removal mechanism comprises at least one electrode in communication with a power supply for generating a DC potential to remove residual ions from the ion optics assembly.

15. The system of claim 14, wherein the ion removal mechanism generates a DC potential creating an electric field that expels the residual ions radially out of the ion optics assembly.

16. The system of claim 14, wherein the ion removal mechanism generates a DC potential creating an axial electric field that expels residual ions out of the ion optics assembly.

17. The system of claim 16, wherein the at least one electrode is selected from the group consisting of LINAC, resistive ion guide, lens electrode stack, ion funnel, and traveling wave ion guide.

18. The system of claim 1, wherein the ion removal mechanism comprises at least one electrode in communication with a power supply for generating a DC potential to accelerate ion motion through the ion optics.

19. A method for analyzing a sample, comprising:
    removing residual ions from an ion optics assembly;
    filtering a first group of ions using an ion mobility filter coupled to a vacuum orifice inlet of a mass analyzer;
    transporting the first group of ions from the ion mobility filter to the mass analyzer using the ion optics assembly; and
    analyzing the first group of ions using the mass analyzer.

20. The method of claim 19, wherein filtering the first group of ions and transporting the first group of ions occur during a first period of time.

21. The method of claim 19, wherein removing residual ions from the ion optics assembly occurs during a second time period.

22. The method of claim 19, wherein the ion mobility filter filters a second group of ions and the ion optics assembly transports the second group of ions from the ion mobility filter to the mass analyzer during a third time period.

23. The method of claim 22, wherein the ion mobility filter is selected from the group consisting of low field mobility separators, high field mobility separators and differential mobility separators.

24. The method of claim 23, wherein the ion mobility filter is selected from the group consisting of FAIMS, DMS, IMS, and DMA.

25. The method of claim 19, wherein the ion mobility filter is located in a first pressure region.

26. The method of claim 25, wherein the mass analyzer is located in a second pressure region different from the first pressure region.

27. The method of claim 26, wherein the ion optics assembly is located in a third pressure region having a pressure intermediate to the pressures in the first and second pressure regions.

28. The method of claim 27, wherein the third pressure region comprises a plurality of different pressure regions.

29. The method of claim 19, wherein the ion optics assembly is selected from the group consisting of multipole array, ring guide, ion funnel and traveling wave device.

30. The method of claim 29 including applying a DC potential to at least two poles of the multipole array configured to remove residual ions from the ion optics assembly.

31. The method of claim 30, including generating an electric field that expels the residual ions away from the ion optics assembly.

32. The method of claim 19, including applying a DC potential to at least one electrode to remove residual ions from the ion optics assembly.

33. The method of claim 32, including generating an electric field that expels the residual ions radially out of the ion optics assembly.

34. The method of claim 32, including generating an axial electric field that expels the residual ions out of the ion optics assembly.

35. The method of claim 34, wherein the at least one electrode is selected from the group consisting of LINAC, resistive ion guide, lens electrode stack, ion funnel, and traveling wave ion guide.

36. The method of claim 19, including applying a DC potential to at least one electrode to accelerate ion motion through the ion optics assembly.

37. The method of claim 19, including decreasing an RF potential within the ion optics assembly to de-focus the ions and remove the ions from the ion optics assembly.

38. A method for analyzing a sample, comprising:
A. filtering, based on ion mobility, a first portion of ions using an ion mobility filter coupled to a vacuum orifice inlet of a mass analyzer and transmitting, using an ion optics assembly, the first portion of ions to the mass analyzer during a first time period;
B. filtering, based on ion mobility, a second portion of ions and transmitting, using the ion optics assembly, the second portion of ions to the mass analyzer during a second time period; and
C. emptying residual ions from at least a portion of the ion optics assembly during a third time period, the third time period occurring between the first and second time periods.

39. The method of claim 38, comprising iteratively repeating steps A-C.

* * * * *